US008609624B2

(12) United States Patent
Nevalainen (10) Patent No.: US 8,609,624 B2
(45) Date of Patent: *Dec. 17, 2013

(54) METHODS AND COMPOSITIONS FOR THE INHIBITION OF STAT5 IN PROSTATE CANCER CELLS

(75) Inventor: Marja T. Nevalainen, Gladwyne, PA (US)

(73) Assignee: Georgetown University, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/477,923

(22) Filed: May 22, 2012

(65) Prior Publication Data
US 2012/0321639 A1    Dec. 20, 2012
US 2013/0183318 A9    Jul. 18, 2013

Related U.S. Application Data

(63) Continuation of application No. 12/548,383, filed on Aug. 26, 2009, now Pat. No. 8,202,849, which is a continuation of application No. 10/554,123, filed as application No. PCT/US2004/012799 on Apr. 23, 2004, now abandoned.

(60) Provisional application No. 60/465,014, filed on Apr. 23, 2003.

(51) Int. Cl.
*A61K 48/00* (2006.01)
*A61K 39/395* (2006.01)
*C12N 15/11* (2006.01)

(52) U.S. Cl.
USPC .................... 514/44 R; 514/44 A; 424/158.1

(58) Field of Classification Search
USPC ........................... 514/44 R, 44 A; 424/158.1
See application file for complete search history.

(56) References Cited

U.S. PATENT DOCUMENTS 8,202,849 B2 * 6/2012 Nevalainen ................ 514/44 A

OTHER PUBLICATIONS

Ahonen et al., "PRL Signal Transduction in the Epithelial Compartment of Rat Prostate Maintained as Long-Term Organ Cultures in Vitro," Endocrinology 143(1):228-238 (2002).
Ahonen et al., "Prolactin Is a Survival Factor for androgen-Deprived Rat Dorsal and Lateral Prostate Epithelium in Organ Culture," Endocrinology 140(11):5412-5421 (1999).
Ahonen et al., "Inhibition of Transcription Factor Stat5 Induces Cell Death of Human Prostate Cancer Cells" J. Biol. Chem. 278(29): 27287-27292 (2003).

Dagvadorj et al., "Autocrine Prolactin Promotes Prostate Cancer Cell Growth via Janus Kinase-2-Signal Transducer and Activator of Transcription-5a/b Signaling Pathway" Endocrinology 148(7):3089-3101.
Gouilleux et al., "Prolactin Induces Phosphorylation of Tyr694 of Stat5 (MGF), a Prerequisite for DNA Binding and Induction of Transcription," The EMBO Journal 13(18):4361-4369 (1994).
Li et al., "Activation of Signal Transducer and Activator of Transcription 5 in Human Prostate Cancer is Associated with High Histological Grade" Cancer Research 64:4774-4782 (2004).
Liu et al., "Cloning and Expression of Stat5 and an Additional Homologue (Stat5b) Involved in Prolactin Signal Transduction in Mouse Mammary Tissue," Proc. Natl. Acad. Sci USA 92:8831-8835 (1995).
Nevalainen et al., "Expression and Hormone Regulation of Prolactin Receptors in Rat Dorsal and Lateral Prostate," Endocrinology 137(7):3078-3088 (1996).
Nevalainen et al., "Basal Activation of Transcription Factor Signal Transducer and Activator of Transcription (Stat5) in Nonpregnant Mouse and Human Breast Epithelium," Molecular Endocrinology 16(5):1108-1124 (2002).
Nevalainen et al., "Hormone Regulation of Human Prostate in Organ Culture," Cancer Research 53:5199-5207 (1993).
Nevalainen et al., "Prolactin and Prolactin Receptors Are Expressed and Functioning in Human Prostate," J. Clin. Invest. 99(4) 618-627 (1997).
Nevalainen et al., "Signal Transducer and Activator of Transcription-5 Activation and Breast Cancer Prognosis" J. Clin. Oncology 22(11): 2053-2060 (2004).
Ni et al., "Selective Activation of Members of the Signal Transducers and Activators of Transcription Family in Prostate Carcinoma," J. Urol., 167(4):1859-62 (2002).
Niidome and Huang "Gene Therapy Progress and Prospects: Nonviral Vectors," Gene Therapy 9:1647-1652 (2002).
Rui et al., "Activation of Receptor-Associated Tyrosine Kinase JAK2 by Prolactin," The Journal of Biological Chemistry 269(7):5364-53698 (1994).
Steger et al., "Neuroendocrine and Reproductive Functions in Male Mice with Targeted Disruption of the Prolactin Gene," Endocrinology 139(9):3691-3695 (1998).
Wennbo et al., "Transgenic Mice Overexpressing the Prolactin Gene Develp Dramatic Enlargement of the Prostate Gland," Endocrinology 138(10):4410-4415 (1997).
Yamashita et al., "Naturally Occurring Dominant-Negative Stat5 Suppresses Transcriptional Activity of Estrogen Receptors and Induces Apoptosis in T47D Breast Cancer Cells," Oncogene 22:1638-1652 (2003).
Yamashita et al., "Naturally Occurring Dominant-Negative StatS Suppresses Transcriptional Activity of Estrogen Receptors and Induces Apoptosis in T47D Breast Cancer Cells," Oncogene 22:1638-1652 (2003).

* cited by examiner

Primary Examiner — Raymond Henley, III
(74) Attorney, Agent, or Firm — Wolf, Greenfield & Sacks, P.C.

(57) ABSTRACT

The present invention relates to compositions and methods for the treatment of prostate cancer. In certain embodiments, the invention relates to compositions and methods for the inhibition of prostate cancer cell growth, comprising inhibiting the activity of Stat5 in prostate cancer cells.

14 Claims, 2 Drawing Sheets

METHODS AND COMPOSITIONS FOR THE INHIBITION OF STAT5 IN PROSTATE CANCER CELLS

RELATED APPLICATIONS

This application is a continuation of U.S. application Ser. No. 12/548,383, filed on Aug. 26, 2009, now U.S. Pat. No. 8,202,849, which is a continuation of U.S. application Ser. No. 10/554,123 filed on Aug. 21, 2006, now abandoned, which is a national stage filing under 35 U.S.C. 371 of International Application PCT/US2004/012799, filed on Apr. 23, 2004, which claims the benefit of priority of U.S. Provisional Application, 60/465,014, filed on Apr. 23, 2003, by Marja Nevalainen, entitled "Inhibition of Transcription Factor Stat5 Induces Cell Death of Human Prostate Cancer Cells". The entire teachings of the referenced Applications are hereby incorporated by reference in their entirety. International Application PCT/US2004/012799 was published under PCT Article 21(2) in English

FUNDING

Work described herein was funded, in whole or in part, by National Institutes of Health Grant Numbers RO1 CA83813 and RO1 DK52013 and Department of Defense Grant DAMD 17-01-1-0059. The United States government has certain rights in the invention.

BACKGROUND OF THE INVENTION

Currently the only pharmacological strategy for the treatment of prostate cancer is ablation of androgens, either as adjuvant therapy after surgery or as a primary therapy for patients who are deemed unfit for surgery. A central clinical problem in prostate cancer treatment is that residual cancer cells inevitably will overcome androgen ablation, and recur as androgen-independent cancer with increased malignancy. Furthermore, for established androgen-independent and metastatic prostate cancer, the only current treatment options are radiation and chemotherapy, which both are relatively ineffective and associated with a number of negative side-effects. Therefore, better treatment strategies for prostate cancer are needed.

SUMMARY OF THE INVENTION

Described herein are compositions and methods for inhibiting cancer cell growth by inhibiting the activity of Stat5 in prostate cancer cells. In certain embodiments, the invention provides a method of inhibiting prostate cancer cell growth, comprising inhibiting Stat5 activity in the prostate cancer cells. Any type of prostate cancer cell, including, for example, primary prostate cancer cells, advanced prostate cancer cells, and metastatic prostate cancer cells, may be employed in the methods and compositions of the subject invention.

In certain embodiments, the invention relates to a method of inhibiting prostate cancer cell growth, comprising inhibiting Stat5 activity in the prostate cancer cells by contacting the prostate cancer cells with an inhibitor of Stat5 activity. In certain embodiments, the contacting the prostate cancer cells with an inhibitor of Stat5 activity results in prostate cancer cell death. In certain embodiments, the inhibitor of Stat5 activity is selected from the group consisting of a small molecule, an siRNA (short interfering RNA) construct, an antisense construct, and an antibody. In further embodiments, the inhibitor of Stat5 activity is a nucleic acid, which encodes a protein that has dominant-negative Stat5 function. In certain embodiments, the protein that has dominant-negative Stat5 function is selected from the group consisting of: mutated Stat5a and mutated Stat5b. Optionally, the mutated Stat5a is Stat5aΔ713. Optionally, the mutated Stat5 is a tyrosine phosphorylation deficient mutant of Stat5 or a DNA-binding deficient mutant of Stat5. In certain embodiments, the inhibitor of Stat5 activity is a nucleic acid, which encodes a protein that has dominant-negative Jak2 function.

In certain embodiments, the agent that inhibits Stat5 activity is an antisense construct.

In yet other embodiments, the subject invention provides a method of inhibiting prostate cancer cell growth, comprising inhibiting Stat5 activity in the prostate cancer cells by contacting the cells with an inhibitor of Stat5 activity that is an siRNA construct. In certain embodiments, the siRNA construct inhibits the activity of a Stat5 polypeptide. In further embodiments, the Stat5 polypeptide is selected from the group consisting of: Stat5a and Stat5b. In additional embodiments, the siRNA construct inhibits the expression of a Stat5 polypeptide, such as a Stat5a or Stat5b polypeptide. In certain embodiments, the siRNA construct comprises Stat5 nucleic acid, such as, for example, Stat5a nucleic acid or Stat5b nucleic acid. In additional embodiments, the siRNA construct comprises Jak2 nucleic acid and inhibits the expression of a Jak2 polypeptide. In certain embodiments, the siRNA construct comprises Jak2 nucleic acid and inhibits the activity of a Jak2 polypeptide The invention additionally relates to a method of inhibiting prostate cancer cell growth, comprising inhibiting Stat5 activity in the prostate cancer cells by contacting the cells with an inhibitor of one or more Stat5 kinases. Examples of Stat5 kinases that may be inhibited are Jak1, Jak2, Jak3, Tyk2, Src, Fyn, Yes, Lck, Hck, Blk, Fgr, and Lyn. In certain embodiments, the inhibitor is a small molecule.

In additional embodiments, the invention provides a method of inhibiting prostate cancer cell growth, comprising inhibiting Stat5 activity in the prostate cancer cells by contacting the prostate cancer cells with an inhibitor of prolactin. Optionally, the prolactin inhibitor is an antibody to a prolactin receptor.

In certain embodiments, the methods and compositions of the invention relate to treating prostate cancer in a male. In certain embodiments, the invention relates to a method of treating prostate cancer in a male in need of such treatment, comprising administering to the male an inhibitor of the activity of Stat5 in prostate cancer cells.

In certain embodiments, the invention provides a method of treating prostate cancer in an male, comprising administering to the male an inhibitor of the activity of Stat5 in prostate cancer cells, wherein the prostate cancer cells are selected from the group consisting of primary prostate cancer cells, advanced prostate cancer cells, and metastatic prostate cancer cells. Primary prostate cancer cells are organ confined. Advanced prostate cancer refers to high histological grade, organ confined prostate cancer cells. Metastatic prostate cancer cells are no longer organ confined.

In additional embodiments of the invention, the invention relates to a method of treating prostate cancer in a male, comprising administering to the male an inhibitor of the activity of Stat5 in prostate cancer cells, wherein the inhibitor of the activity of Stat5 is selected from the group consisting of a small molecule, an siRNA construct, an antisense construct, and an antibody.

The invention also provides a method of diagnosing or aiding in the diagnosis of prostate cancer in a male, comprising obtaining a sample of prostate tissue from a male and determining whether activated Stat5 is present in cells of the prostate tissue sample, wherein the presence of activated Stat5 is an indication of prostate cancer in the male. In certain embodiments, the prostate cancer is primary prostate cancer, advanced prostate cancer or metastatic prostate cancer. In additional embodiments of the invention, activated Stat5 is detected by means of a method selected from the group consisting of immunohistochemistry, immunocytochemistry and DNA-binding assays. In certain embodiments of the invention, the activated Stat5 detected is nuclear Stat5.

In further embodiments, the invention provides a method of treating prostate cancer in a male, comprising administering to a male in need of treatment thereof a therapeutically effective amount of an agent (drug) that inhibits the activity of Stat5 in prostate cancer cells, wherein the activity of Stat5 is inhibited in prostate cancer cells of the male. In certain embodiments, the prostate cancer is primary prostate cancer, advanced prostate cancer, or metastatic prostate cancer. In additional embodiments, the inhibitor of the activity of Stat5 is selected from the group consisting of a small molecule, an siRNA construct, an antisense construct, and an antibody.

In other embodiments, the invention relates to a method of treating prostate cancer in a male, comprising administering to a male in need of treatment thereof a therapeutically effective amount of an agent that inhibits the activity of Stat5 in prostate cancer cells, wherein the activity of Stat5 is inhibited in prostate cancer cells of the male. In certain embodiments, the invention provides an inhibitor of Stat5 that is a nucleic acid, which encodes a protein that has dominant-negative Stat5 function. In certain embodiments, the protein encoded is selected from the group consisting of mutated Stat5a and mutated Stat5b. Optionally, the mutated Stat5 a is Stat5aΔ713. Optionally, the mutated Stat5 is a tyrosine phosphorylation deficient mutant of Stat5 or a DNA-binding deficient mutant of Stat5. In certain embodiments, the invention provides an inhibitor of Stat5 that is a nucleic acid, which encodes a protein that has dominant-negative Jak2 function.

In certain embodiments of the invention, an agent that inhibits Stat5 activity is an antisense construct.

In additional embodiments, the invention relates to the inhibition of Stat5 activity through the use of siRNA. For example, siRNAs of the invention are effective in silencing nucleic acid molecules which include Stat5 nucleic acid (e.g., mRNA) as well as the nucleic acid (e.g., mRNA) of activators of Stat5, including Stat5 kinases, such as Janus kinase-2 (Jak2). The siRNA is effective in silencing a nucleic acid molecule (e.g., interfering with or preventing the expression of a gene or gene product), which nucleic acid molecule encodes, for example, a Stat5 polypeptide. The terms peptides, proteins and polypeptides are used interchangeably herein. In certain embodiments, an siRNA construct of the invention is effective in inhibiting the activity of a Stat5 polypeptide. In further embodiments, the Stat5 polypeptide is selected from the group consisting of Stat5a and Stat5b. In certain embodiments, an siRNA construct of the invention is effective in inhibiting the expression of a Stat5 polypeptide. In further embodiments, an siRNA construct of the invention is effective in inhibiting the expression of a Stat5 polypeptide selected from the group consisting of Stat5a and Stat5b. In further embodiments, the invention relates to an siRNA construct that is directed to Stat5 nucleic acid (e.g., mRNA), such as Stat5 nucleic acid selected from the group consisting of Stat5a nucleic acid and Stat5b nucleic acid.

In yet other embodiments, the invention provides a method of treating prostate cancer in a male, comprising administering to a male in need of treatment thereof a therapeutically effective amount of an agent that inhibits the activity of Stat5 in prostate cancer cells, wherein the activity of Stat5 is inhibited in prostate cancer cells of the male and wherein Stat5 activity is reduced through the inhibition of one or more Stat5 kinases. In further embodiments, the invention relates to inhibition of a Stat5 kinase selected from the group consisting of Jak1, Jak2, Jak3, Tyk2, Src, Fyn, Yes, Lck, Hck, Blk, Fgr, and Lyn. In certain embodiments of the invention, an inhibitor of one or more Stat5 kinases is a small molecule. In other embodiments, an inhibitor of Stat5 is a nucleic acid, which encodes a protein that has dominant negative Jak2 function.

In further embodiments, the invention provides a method of treating prostate cancer in a male, comprising administering to a male in need of treatment thereof a therapeutically effective amount of an agent that inhibits the activity of Stat5 in prostate cancer cells, wherein the activity of Stat5 is inhibited in prostate cancer cells of the male and wherein Stat5 activity is reduced through the inhibition of prolactin. In certain embodiments of the invention, Stat5 activity is reduced through inhibition of prolactin by an antibody to a prolactin receptor.

In further embodiments, the invention provides a method of treating prostate cancer in a male, comprising administering to a male in need of treatment thereof a therapeutically effective amount of an agent that inhibits the activity of Stat5 in prostate cancer cells, wherein the activity of Stat5 is inhibited in prostate cancer cells of the male and wherein inhibition of the activity of Stat5 in prostate cancer cells of the male results in prostate cancer cell death.

The invention additionally relates to a method for identifying an agent that inhibits Stat5 activity in prostate cancer cells, comprising (a) contacting a prostate cancer cell or tissue sample comprising prostate cancer cells with a candidate agent and (b) determining the effect of the agent in (a) on the activity of Stat5, wherein if there Stat5 activity determined in (b) is less than Stat5 activity in an appropriate control sample, an inhibitor of Stat5 activity is identified. A control sample is an equivalent sample of prostate cancer cells or tissue comprising prostate cancer cells in which Stat5 is activated, which cells or tissue samples have not been treated with the candidate agent. A test sample is equivalent to the control sample except that it is contacted with a candidate agent. For example, the cells or tissues samples of (a) are test samples. A control may be run simultaneously with the test sample, or it may be pre-established.

In further embodiments, the invention provides a diagnostic method for predicting responsiveness to Stat5 inhibition therapy for treatment of prostate cancer, comprising (a) obtaining a sample of prostate tissue from a male in need of treatment for prostate cancer and (b) determining whether activated Stat5 is present in cells of the prostate tissue sample, wherein if activated Stat5 is present, it is predictive of responsiveness to Stat5 inhibition therapy for treatment of prostate cancer. In certain embodiments, the prostate cancer is primary prostate cancer, advanced prostate cancer, or metastatic prostate cancer.

In additional embodiments, the invention relates to the use of an inhibitor of Stat5 activity to prepare a medicament to inhibit prostate cancer cell growth. In further embodiments, the invention relates to the use of an inhibitor of Stat5 activity to prepare a medicament to treat prostate cancer in a male in need of treatment thereof.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, Current Protocols in Cell Biology, ed. by Bonifacino, Dasso, Lippincott-Schwartz, Harford, and Yamada, John Wiley and Sons, Inc., New York, 1999; Gene Targeting: A Practical Approach, IRL Press at Oxford University Press, Oxford, 1993; Gene Targeting Protocols, Human Press, Totowa, N.J., 2000; Molecular Cloning A Laboratory Manual, 2nd Ed., ed. by Sambrook, Fritsch and Maniatis (Cold Spring Harbor Laboratory Press: 1989); Culture Of Animal Cells (R. I. Freshney, Alan R. Liss, Inc., 1987); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987).

Other features and advantages of the invention will be apparent from the following detailed description, and from the claims.

DETAILED DESCRIPTION OF THE DRAWINGS

DETAILED DESCRIPTION OF THE INVENTION

Described herein are compositions and methods for inhibiting the growth of prostate cancer cells by inhibiting Stat5 activity. The methods and compositions of the present invention can be used in relation to any type of prostate cancer cell, including, for example, primary prostate cancer cells, advanced prostate cancer cells, and metastatic prostate cancer cells.

In certain embodiments, the subject invention relates to methods and compositions for treating prostate cancer in a male. In certain embodiments, the invention relates to a method of treating prostate cancer in a male, comprising administering to the male an inhibitor of the activity of Stat5 in prostate cancer cells.

Identifying regulators of prostate cancer cell survival may lead to new therapeutic strategies for prostate cancer. Applicants report prevalent activation of transcription factor Stat5 in human prostate cancer and provide novel evidence that blocking activation of Stat5 in human prostate cancer cells leads to extensive cell death. Specifically, Stat5 was activated in 65% of human prostate cancer specimens examined based on nuclear location of tyrosine phosphorylated Stat5. Adenoviral gene delivery of a dominant-negative Stat5 mutant (DNStat5), but not wild-type Stat5, induced cell death of both the androgen-independent human prostate cancer cell line CWR22Rv and the androgen-sensitive LnCap cell line. Endogenous Stat5 was active in both CWR22Rv and LnCap cells. In contrast, only low levels of inactive Stat5 proteins were detected in the PC-3 cell line, which correlated with resistance to DNStat5-induced cell death. In CWR22Rv and LnCap cells, inhibition of Stat5 by expression of DNStat5 induced apoptotic cell death, as judged from morphological changes, DNA fragmentation, and Caspase-3 activation, with evidence of a Caspase-9 dependent mechanism. Applicants propose that blocking Stat5 function may represent a novel therapeutic approach for prostate cancer.

Prostate cancer typically progresses to androgen-independent growth after androgen-ablation therapy. Identification of androgen-independent proteins that control prostate cancer cell survival may lead to more effective therapies. Using long-term organ cultures of human and rat prostate tissues, Applicants have documented direct effects of prolactin (Prl) as a mitogen and survival factor for prostate epithelium (1-4). These observations have been complemented by demonstration of massive hyperplasia of prostates in transgenic mice over-expressing Prl (5,6), as well as reduced prostate sizes in Prl-null mice (7). Importantly, Applicants have also shown local production of Prl (1,8) and expression of Prl-receptors in prostate epithelium (1,9) and, thereby, provided evidence for an autocrine loop of Prl action in prostate. Downstream of Prl-receptor activation, Applicants have demonstrated that Stat5 is a key signaling protein in normal rat prostate epithelium (10), and that deficiency of Stat5 in Stat5a-null mice is associated with defective prostate tissue architecture (11).

Stat5 is one of 7 members of the Stat family of transcription factors in mammals (12), and consists of two distinct; but highly homologous, proteins, the 94-kDa Stat5a and 92-kDa Stat5b (13,14). In response to Prl, Stat5a and Stat5b become activated by phosphorylation on residue Tyr694 and Tyr699, respectively, in the C-terminal domain predominantly by Janus tyrosine kinase-2 (Jak2), which is preassociated with the cytoplasmic domain of the Prl receptor (15). Tyrosine phosphorylated Stat5 proteins dimerize and translocate to the nucleus, where they bind to specific response elements of target gene promoters to regulate transcription (16).

Based on previous findings of a survival function of Prl in normal prostate epithelium (4), an autocrine production of Prl by prostate epithelial cells (1,8), and the glandular defect of the prostates of Stat5a knock-out mice (11), Applicants hypothesized that Stat5 may act as a survival protein in human prostate cancer, and that blocking Stat5 function could induce death of prostate cancer cells. Applicants investigated activation of Stat5 in 40 human prostate cancer samples by immunohistochemical analysis using activation-state specific anti-phosphoTyrStat5 antibody. To specifically block Stat5 activity in human prostate cancer cells, Applicants created a dominant-negative mutant of Stat5 (DNStat5) in an adenoviral transfer vector. As described herein, Applicants demonstrate that transcription factor Stat5 is activated in a significant number of human prostate cancer specimens and that blocking stats activity induces extensive apoptosis of prostate cancer cells.

The Signal Transducer and Activator of Transcription (STAT) family of transcription factors provide a signaling link between cell surface hormone and cytokine receptors and specific response elements in the promoters of selective genes. Seven mammalian STAT genes have been identified. The Stat5 transcription factor is involved in regulation of cell growth, differentiation, and cell survival based on data in breast epithelial cells and cells of the lymphohematopoietic system (Wakao, Gouilleux et al. 1994). Stat5 exists as two highly homologous isoforms, Stat5a and 5b, which have more than 95% amino acid homology and are encoded by separate genes (Liu, Robinson et al. 1995; Grimley, Dong et al. 1999). Stat5 is required for normal mammary epithelial cell development and differentiation (Liu, Robinson et al. 1997; Udy, Towers et al. 1997; Moriggl, Topham et al. 1999).

Stat5 polypeptides typically are cytoplasmic and quiescent under homeostatic conditions. Their activation results from phosphorylation of the highly conserved C-terminal tyrosine at Tyr694 in Stat5a or the corresponding Tyr699 in Stat5b by certain intracellular tyrosine kinases. This phosphorylation permits dimer pair formation, which is needed for Stat5 to bind to DNA.

This initial phosphotyrosyl "on-switch" is a generic Stat feature (Darnell 1997; Darnell 1998) and is triggered when cells with cognate receptors are exposed to a variety of stimuli including cytokines, immune complexes, microbiologic agents or non-peptidyl compounds. Although the spectrum of agonists thus is heterogeneous, the bulk implicated in triggering Stat5 activation belong to the class I and class II cytokine superfamilies. (See Table 4 of (Grimley, Dong et al. 1999). These cytokines utilize receptors lacking a catalytic domain (Liu, Gaffen et al. 1998), so that the Stat activation is most often dependent upon an auxiliary protein kinase (Leonard and O'Shea 1998).

The Janus tyrosine kinases (Jaks) form biochemically stable associations with class I and class II cytokine receptors. A non-covalent linkage facilitates Jak phosphorylations during receptor ligation and increases the odds of interactions between Jaks and Stats recruited to receptor-Jak complexes (Leonard and O'Shea 1998). This critical and conserved mutual relationship has engendered the scientific vernacular of "Jak-Stat pathway" (Liu, Gaffen et al. 1998). However, Jaks are not the sole means of Stat activation.

Stat5a and Stat5b can also be tyrosine phosphorylated by a number of cytokines commonly designated as "growth factors" which bind to receptor tyrosine kinases (RTKs). The RTKs possess intrinsic catalytic properties, and may trigger Stat5 signals absent a direct linkage to the Jak enzyme system (Chen, Sadowski et al. 1997). In addition, Stat5 tyrosine phosphorylation might be effected by cytosolic protein kinases in the Src or Tec families. As "nonreceptor tyrosine kinases" (NTKs), the latter enzymes can function without extrinsic stimulation due to receptor ligation. The Src-family kinase Lck has been implicated in Stat5 phosphorylation during T cell proliferation (Welte, Leitenberg et al. 1999) and constitutively active NTKs, RTKs or analogous oncoproteins may be particularly significant in maintaining a constitutive phosphorylation of Stat5 in autonomously proliferating neoplastic cells (For example, See (Lacronique, Boureux et al. 1997; Wellbrock, Geissinger et al. 1998)).

In addition to the initial activation switch of Stat5, which involves phosphorylation of a tyrosine residue within a conserved C-terminal segment and causes dimerization of Stat5 molecules (Gouilleux, Wakao et al. 1994), a second coordinated activation event is required for functional activation. This involves translocation of dimerized Stat5 from the cytoplasm into the cell nucleus, which permits Stat5 to come in proximity of and bind to gene regulatory promoter elements, and thus regulate transcription of specific genes (Gouilleux, Wakao et al. 1994; Kazansky, Kabotyanski et al. 1999). Because Stat5 not only requires phosphorylation of a specific tyrosine residue, but also needs to translocate into the cell nucleus in order to function as an active DNA-binding transcription factor, amounts of tyrosine phosphorylated Stat5 located within the cell nucleus will reflect the levels of activated Stat5 more accurately than overall cellular levels of tyrosine phosphorylated Stat5. For instance, tyrosine phosphorylation of Stat5a by the Src tyrosine kinase has been shown not to be accompanied by nuclear translocation (Kazansky, Kabotyanski et al. 1999), illustrating that quantitation of tyrosine phosphorylation status alone without assessing nuclear localization is not sufficient for accurate determination of levels of activated Stat5. Correspondingly, Stat transcription factors may become dephosphorylated within the cell nucleus and lose the ability to bind to DNA (Haspel and Darnell 1999), making assays that detect nuclear Stat5 protein levels alone also not sufficient for accurate determination of levels of activated Stat5. In the present application, the term "levels of activated Stat5" refers to levels of tyrosine phosphorylated Stat5 within the cell nucleus.

Antibodies that bind exclusively to tyrosine phosphorylated Stat5 can be used to detect activated Stat5 in the nuclei of cells by immunocytochemistry or immunohistochemistry, provided that proper steps are taken to achieve antigen retrieval of this cryptic antigenic site. This antigenic site is cryptic, or unavailable, unless the phosphorylated tyrosine bound to the SH2 domain of the partner molecule in the dimer is dissociated by specific treatment.

Detection of active, tyrosine phosphorylated Stat5 by immunohistochemistry in tissue sections has been reported (Jones, Welte et al. 1999; Ahonen, Harkonen et al. 2002; Nevalainen, Xie et al. 2002). The extent to which Stat5 promotes cell proliferation, cell survival, or inhibits growth by inducing cell differentiation in various tissues, including prostate gland, is unresolved. The possibility that inhibiting Stat5 function would induce cell killing in human prostate cancer, or that Stat5 activation status in prostate cancer is of predictive value for Stat5-suppressive prostate cancer treatment, was not obvious prior to the inventors' discovery, because a priori, it had been argued that Stat5 was not activated in human prostate cancer (Ni, Lou et al. 2002). Therefore, the present invention and description of a new therapy for prostate cancer based on inhibiting or blocking that activity of Stat5 was unexpected based on the published literature and prevailing views within the scientific field. As such, the role of Stat5 in human prostate cancer development and progression had not been established, and its use as a marker of therapeutic response to the new therapy of human prostate cancer had not been reported.

Applicants have invented a new strategy to induce apoptotic cell death of prostate cancer cells by inhibition of transcription factor Stat5. This discovery can be used for development of a new therapy for prostate cancer.

The concept of transcription factor Stat5 as a survival factor and therapeutic target in prostate cancer is completely novel and unexpected. Specifically, a study by Gao and colleagues (Ni, Lou et al. 2002) indicated that in human prostate tissue homogenates there was only a low level of Stat5 binding to an oligonucliotide probe corresponding to the Stat5 response element of the beta-casein promoter in electrophoretic mobility shift assay (EMSA). However, using a highly sensitive in situ immunohistochemical detection technique (Nevalainen, Xie et al. 2002), which detects Stat5 activation at a single cell level, Applicants have now demonstrated that Stat5 is activated in human prostate cancer with high frequency. This finding corresponds technically to observations in human and mouse mammary gland where activation of Stat5 was difficult to detect outside pregnancy by EMSA assay using tissue homogenates, but was readily detectable by immunohistochemical detection of activated Stat5 at single cell level (Nevalainen, Xie et al. 2002).

The novel finding of Stat5 activation in human prostate cancer, combined with previous studies (Nevalainen, Valve et al. 1996; Nevalainen, Valve et al. 1997; Nevalainen, Valve et al. 1997; Ahonen, Harkonen et al. 1999; Nevalainen, Ahonen et al. 2000; Ahonen, Harkonen et al. 2002) led Applicants to test whether inhibition of Stat5 would induce cell death of human prostate cancer cells. However, in light of the published report by Gao et al (Ni, Lou et al. 2002) it was completely unexpected that blocking Stat5 activity would induce cell killing.

Applicants have also discovered that detection of activated Stat5 in prostate cancer can predict responsiveness to the therapeutic strategy of the invention based on inhibition of transcription factor Stat5.

This is based on the correlation between endogenous Stat5 activation in prostate cancer cell lines and their sensitivity to inhibition of Stat5 activity. Specifically, dominant-negative Stat5 gene therapy induced cell killing in cells where endogenous Stat5 was active (e.g. CWR22, LNCaP) but not in cells where endogenous Stat5 was not active (e.g. PC-3). Therefore, a sensitive method that detects active Stat5 in prostate cancer cells, surgical biopsy or specimen, is expected to predict responsiveness to the new therapy. Predicting responsiveness is important so that patients can be selected who may benefit from the therapy, while patients whose tumors are deemed unresponsive, may not need to undergo this treatment.

In additional embodiments, the invention provides for the detection of activated Stat5 by methods including immunohistochemistry of activated Stat5, immunohistochemical detection of nuclear Stat5, and DNA-binding assay of Stat5 for prediction of responsiveness of a male with prostate cancer for therapy based on inhibition of Stat5. "Inhibition of Stat5 therapy" refers to therapy based on the inhibition of Stat5 activity. For example, in certain embodiments of the present invention, inhibition of Stat5 therapy includes inhibiting the activity of Stat5a and/or Stat5b polypeptides in a prostate cancer cell in a male in need of treatment for prostate cancer. Inhibition of Stat5 therapy further includes inhibiting the expression of Stat5 (e.g., Stat5a and/or Stat5b) polypeptides in a prostate cancer cell. Inhibition of Stat5 therapy can be applied to any type of prostate cancer cell, including, for example, primary prostate cancer cells, advanced prostate cancer cells, and metastatic prostate cancer cells.

In certain embodiments, the invention relates to agents that inhibit Stat5 activity. Inhibitors of Stat5 include agents that inhibit the expression of a Stat5 polypeptide. Inhibitors of Stat5 also include agents that inhibit Stat5 activity. For example, such inhibitors include those agents that inhibit activation of Stat5, such as agents that inhibit Stat5 tyrosine phosphorylation and/or translocation of phosphorylated Stat5 into the nucleus.

In certain embodiments, the present invention contemplates inhibiting Stat5 in prostate cancer cells by inhibiting one or more of the molecules involved in Stat5 activation. For example, inhibitors of the invention include agents that inhibit one or more of the molecules involved in e.g., Stat5 phosphorylation (e.g., tyrosine phosphorylation), Stat5 translocation to the nucleus, and/or Stat5 binding to DNA. Molecules involved in Stat5 activation include molecules, such as tyrosine kinases (e.g., Jak2), that interact directly with Stat5. Molecules involved in Stat5 activation also include molecules, such as prolactin, that interact indirectly with Stat5.

Inhibitors of the invention include agents that inhibit phosphorylation of Stat5. For example, agents with phosphatase activity toward phosphorylated Stat5 are inhibitors of Stat5 that may be employed in the methods of the present invention. Examples of phosphatases include alkaline phosphatase, potato acid phosphatase, protein phosphatase 2A, and protein tyrosine phosphatase-1B (PTP-1B) (see suppliers such as, e.g., Amersham Biosciences, Sigma, and Calbiochem).

Inhibitors of the invention further include agents that inhibit Stat5 tyrosine kinases, such as, for example, Jak2 inhibitors (e.g., tyrphostin B42, supplied by e.g., Calbiochem) and Jak3 inhibitors (e.g., PNU156804 described in Stepkowski, S M et al (2002) Blood 99(2):680-689). Inhibitors of Jak1 and Tyk2 are also contemplated by the present invention.

Inhibitors of the invention additionally include agents that inhibit activators of Stat5 such as inhibition of various growth factors and non-receptor tyrosine kinases. For example, inhibitors of any of the Src family tyrosine kinases are contemplated by the present invention as inhibitors of Stat5 activity in prostate cancer cells. Examples of Src family kinases include Src, Fyn, Yes, Lck, Hck, Blk, Fgr, and Lyn. An example of an inhibitor of Src family tyrosine kinases includes PP2 (supplied by e.g., Calbiochem).

Inhibitors of the invention further include agents that inhibit DNA binding of Stat5. This may be achieved through the use of an electrophilic inhibitor. Examples of electrophilic inhibitors include disulfide benzamides and benzisothiazolone derivatives as described in Wang, L H et al (2004) Nat Med 10:40-47.

In certain embodiments, the invention relates to agents that inhibit Stat5 activity that are proteins that have dominant-negative Stat5 function. Such proteins include, but are not limited to, mutated Stat5a or Stat5b, or genetic engineering of other related Stat genes, in whole or in part, that would effectively result in dominant-negative function towards the activity of Stat5a and/or Stat5b. This would not be limited to the Stat5aΔ713 mutant as described herein, but also other modifications of Stat5a or Stat5b. Other variants of Stat5a or Stat5b have been reported to act as dominant-negative Stat5 molecules (Yamashita, Iwase et al. 2003). Additionally, agents that inhibit Stat5 activity include gene products that result in dominant-negative function towards the activity of Sta5a and/or Stat5b such as, for example, mutated Jak2 genes, which encode dominant-negative Jak2 polypeptides. Additionaly, in certain embodiments, the invention relates to other variants of Stat5 such as tyrosine phosphorylation deficient mutants of Stat5 or DNA binding deficient mutants of Stat5.

Therapeutic use of molecules that inhibit Stat5 activity include nucleic acids for delivery to prostate cancer cells, either by viral or non-viral vectors. In certain embodiments, the invention relates to Stat5 antisense therapy, using either oligonucleotide-based or gene expression-based vectors; siRNA for Stat5, either oligonucleotide-based or gene expression-based vectors; and small-molecule pharmacological inhibitors of Stat5 tyrosine kinase(s), such as, for example, inhibitors of Jak2.

In certain embodiments of the invention, Stat5 activity is inhibited through the use of antisense, ribozyme, RNAi, and other nucleic acid-related methods and compositions for inhibiting a Stat5 activity. Any of the nucleic acid therapies of the invention may be designed to target a nucleic acid sequence represented in a Stat5 nucleic acid, such as Stat5 nucleic acid disclosed in GenBank Accession Nos. NM__003152 and NM__012448. In certain embodiments, any of the nucleic acid therapies of the invention may be designed to target a nucleic acid sequence represented in a nucleic acid sequence of a molecule involved in the activation of Stat5, such as, for example, Jak2 nucleic acid. sequence disclosed in GenBank Accession No. NM__004972.

The term "RNA interference" or "RNAi" refers to any method by which expression of a gene or gene product is decreased by introducing into a target cell one or more double-stranded RNAs which are homologous to the gene of interest (particularly to the messenger RNA of the gene of interest). RNAi may also be achieved by introduction of a DNA:RNA hybrid wherein the antisense strand (relative to the target) is RNA. Either strand may include one or more modifications to the base or sugar-phosphate backbone. Any nucleic acid preparation designed to achieve an RNA interference effect is referred to herein as an siRNA construct. SiRNA includes short hairpin RNA (shRNA).

Certain embodiments of the invention make use of materials and methods for effecting knockdown of one or more Stat5 genes by means of RNAi. Additional embodiments of the invention make use of materials and methods for effecting knockdown of one or more genes involved in the activation of Stat5, such as, for example, Jak2. RNAi is a process of sequence-specific post-transcriptional gene repression which can occur in eukaryotic cells. RNAi has been shown to be effective in reducing or eliminating the expression of genes in a number of different organisms including *Caenorhabditiis elegans* (see e.g., Fire et al. (1998) Nature 391: 806-11), mouse eggs and embryos (Wianny et al. (2000) Nature Cell Biol 2: 70-5, Svoboda et al. (2000) Development 127: 4147-56), and cultured RAT-1 fibroblasts (Bahramina et al. (1999) Mol Cell Biol 19: 274-83), and appears to be an anciently evolved pathway available in eukaryotic plants and animals (Sharp (2001) Genes Dev. 15: 485-90), RNAi has proven to be an effective means of decreasing gene expression in a variety of cell types including HeLa cells, NIH/3T3 cells, COS cells, 293 cells and BHK-21 cells.

The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides of the application may include 3' overhang ends. dsRNAs may be synthesized chemically or produced in vitro or in vivo using appropriate expression vectors. Synthetic RNAs include 21 nucleotide RNAs chemically synthesized using methods known in the art (e.g., Expedite RNA phophoramidites and thymidine phosphoramidite (Proligo, Germany). Synthetic oligonucleotides may be deprotected and gel-purified using methods known in the art (see e.g., Elbashir et al. (2001) Genes Dev. 15: 188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence. Any of the above RNA species may be designed to include a portion of nucleic acid sequence represented in a Stat5 nucleic acid, such as Stat5 nucleic acid disclosed in GenBank Accession Nos. NM__003152 and NM__012448. RNAi constructs of the invention further include RNAi constructs designed to include a portion of nucleic acid sequence represented in a gene involved in the activation of Stat5, such as, for example, Jak2. Methods and compositions for designing appropriate oligonucleotides may be found, for example, in U.S. Pat. No. 6,251,588, the contents of which are incorporated herein by reference. Further compositions, methods and applications of RNAi technology are provided in U.S. Pat. Nos. 6,278,039, 5,723,750 and 5,244,805, which are incorporated herein by reference.

In further embodiments, the invention relates to the use of isolated "antisense" nucleic acids to inhibit expression, e.g., by inhibiting transcription and/or translation of a Stat5 nucleic acid. The antisense nucleic acids may bind to the potential drug target by conventional base pair complementarity, or, for example, in the case of binding to DNA duplexes, through specific interactions in the major groove of the double helix. In general, these methods refer to the range of techniques generally employed in the art, and include any methods that rely on specific binding to oligonucleotide sequences.

The antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides or agents facilitating transport across the cell membrane (see, e.g., Letsinger et al., 1989, Proc. Natl. Acad. Sci. U.S.A. 86:6553-6556, Lemaitre et al., 1987, Proc. Natl. Acad. Sci. 84:648-652, PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6:958- 976) or intercalating agents. (see, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

In certain embodiments, the invention relates to other nucleic acid therapies to inhibit the activity of Stat5 in prostate cancer cells, including ribozymes, which are enzymatic RNA molecules capable of catalyzing the specific cleavage of RNA. (For a review, see Rossi (1994) Current Biology 4: 469-471) and DNA enzymes. Ribozyme molecules designed to catalytically cleave Stat5 mRNA transcripts can also be used to prevent translation of subject Stat5 mRNAs and/or expression of Stat5 polypeptides. (See, e.g., PCT International Publication WO90/11364, published Oct. 4, 1990, Sarver et al. (1990) Science 247:1222-1225 and U.S. Pat. No. 5,093,246). DNA enzymes are designed so that they recognize a particular target nucleic acid sequence, much like an antisense oligonucleotide, however much like a ribozyme they are catalytic and specifically cleave the target nucleic acid. Methods of making and administering DNA enzymes can be found, for example, in U.S. Pat. No. 6,110,462.

RNAi, antisense, ribozyme, and DNA enzyme molecules of the application may be prepared by any method known in the art for the synthesis of DNA and RNA molecules. These include techniques for chemically synthesizing oligodeoxyribonucleotides and oligoribonucleotides such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Agents contemplated by the invention also include compounds selected from libraries of potential inhibitors of Stat5. There are a number of different libraries used for the identification of small molecule inhibitors, including: chemical libraries, natural product libraries, and combinatorial libraries comprised of random peptides, oligonucleotides or organic molecules.

A wide variety of chemical libraries may be used. For example, chemical libraries may be used that comprise random chemical structures, some of which are analogs of known compounds or analogs of compounds that have been identified as "hits" or "leads" in other drug discovery screens, some of which are derived from natural products, and some of which arise from non-directed synthetic organic chemistry.

Natural product libraries include collections of products of microorganisms, animals, plants, or marine organisms that are used to create mixtures for screening. Natural product libraries include polyketides, non-ribosomal peptides, and variants (non-naturally occurring) thereof (reviewed in Science 282: 63-68 (1998)). Combinatorial libraries include those composed of large numbers of peptides, oligonucleotides, or organic compounds as a mixture. Combinatorial libraries include non-peptide combinatorial libraries. Still other combinatorial libraries include peptide, protein, peptidomimetic, multiparallel synthetic collection, recombinatorial, polypeptide, antibody, and RNAi libraries. For a review of combinatorial chemistry and libraries created therefrom, see Myers, Curr. Opin. Biotechnol. 8: 701-707 (1997). Identification of inhibitors through use of the various libraries described herein permits modification of the candidate "hit" or "lead" to optimize the capacity of the "hit" to modulate activity.

Antibodies can be used as modulators of the activity of a particular protein, such as, for example Stat5 or receptors for prolactin. Antibodies can have extraordinary affinity and specificity for particular epitopes. Antibodies can bind to a particular protein in such a way that the binding of the antibody to the epitope on the protein can interfere with the function of that protein. For example, an antibody may inhibit the function of a Stat5 polypeptide by sterically hindering the proper interactions between the Stat5 polypeptide and another protein or proper interactions with other molecules, or occupying active sites. Alternatively the binding of the antibody to an epitope on the particular protein may alter the conformation of that protein such that it is no longer able to properly function. Both monoclonal and polyclonal antibodies (Ab) directed against a particular polypeptide, such as a Stat 5 polypeptide or a prolactin receptor polypeptide, and antibody fragments such as Fab, F(ab)2, Fv and scFv can be used to block the action of a particular protein, such as Stat5.

Monoclonal or polyclonal antibodies can be made using standard protocols (see, e.g., Antibodies: A Laboratory Manual ed. by Harlow and Lane (Cold Spring Harbor Press: 1988). A mammal, such as a mouse, a hamster, a rat, a goat, or a rabbit can be immunized with an immunogenic form of the peptide.

Variant polypeptides and peptide fragments can agonize or antagonize the function of a particular protein, such as the function of Stat5. Examples of such variants and fragments include constitutively active or dominant negative mutants of a particular protein, such as dominant negative mutants of Stat5 or Jak2 as described herein. Antagonistic variants may function in any of a number of ways, for example, as described herein. One of skill in the art can readily make variants comprising an amino acid sequence at least 60%, 70%, 75%, 80%, 85%, 90%, 95%, 98% $_{or}$ 99% identical to a particular polypeptide, or a fragment thereof, and identify variants that agonize or antagonize the function of Stat5. Similarly, one can make peptide mimetics (e.g., peptidomimetics) that agonize or antagonize the function of a Stat5 polypeptide.

Toxicity and therapeutic efficacy of agents (drugs, compounds) of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue, such as the prostate, in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound used in the methods of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humanns. Levels in plasma may be measured, for example, by high performance liquid chromatography.

Pharmaceutical compositions for use in accordance with the present invention may be formulated in a conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For example, in certain embodiments, a composition of the invention comprises an RNAi mixed with a delivery system, such as a liposome system, and optionally including an acceptable excipient.

For such therapy, the compounds of the application can be formulated for a variety of loads of administration, including systemic and topical or localized administration. Techniques and formulations generally may be found in Remmington's Pharmaceutical Sciences, Meade Publishing Co., Easton, Pa. Agents of the invention may be administered systemically, including injection intramuscularly, intravenously, intraperitoneally, and subcutaneously. Systemic administration can also be by transmucosal or transdermal means. Transmucosal administration may be through nasal sprays or using suppositories.

Agents of the invention may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Agents of the invention may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For therapies involving the administration of nucleic acids, the oligomers of the application can be formulated for a variety of modes of administration, including systemic and topical or localized administration. For systemic administration, the agents may be injected, including intramuscularly, intravenously, intraperitoneally, intranodally, and subcutaneously for injection. The oligomers of the application can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

The invention now being generally described, it will be more readily understood by reference to the following examples, which are included merely for purposes of illustration of certain aspects and embodiments of the present invention, and are not intended to limit the invention.

EXAMPLIFICATION

Materials and Methods

Cell Culture. CWR22Rv, LnCap, and PC-3 cells (ATCC, Manassas, Va.) were cultured in RPMI-1640 medium (Biofluids, Gaithersburg, Md.) and T47D cells (ATCC) in DMEM containing 10% fetal calf serum, 2 mM L-glutaniine, and penicillin-streptomycin (50 IU/ml and 50 µg/ml, respectively) at 37° C. with 5% $CO_2$. LnCap cells were cultured in the presence of 1 nM dihydrotestosterone (5α-androstan-17β-ol-3-one; Sigma, Chemical Co., MO).

Immunohistochemical Detection of Phosphorylated Stat5 in Human Prostate Cancer.

Tissue sections of formalin-fixed prostate cancer samples from 40 patients were immunostained for activated Stat5 as described previously (17). Briefly, tissue sections were de-paraffinized in xylene followed by re-hydration in graded alcohol. To unmask the epitopes, the slides were microwave-treated with antigen retrieval solution AxAR1 (Advantex BioReagents, Conroe, Tex.) or AxAR2 for use with anti-pTyrStat5 mAb or anti-panStat5 mAb, respectively. Endogenous peroxidase activity was blocked by incubating the slides in 0.3% hydrogen peroxide, and the tissue sections were incubated in normal goat serum (BioGenex Laboratories Inc., San Ramon, Calif.) for 2 h to block unspecific binding of immunoglobulins (IgGs). The anti-pTyrStat5 mAb was diluted in 1% BSA in PBS at a final concentration of 0.6 µg/ml (Advantex BioReagents). The anti-panStat5 mAb was used at a concentration of 2 µg/ml (Advantex Bioreagents). Antigen-antibody complexes were detected using anti-mouse biotinylated goat secondary antibody followed by streptavidin-horseradish-peroxidase complex (BioGenex). 3,3'-di-aminobenzidine was used as chromogen and hematoxylin as counterstain. For negative controls, parallel slides were immunostained with subtype-specific mouse IgG, and lactating human mammary gland was used as positive control tissue (17).

Generation of Adenovirus for Gene Delivery of Dominant-Negative and Wild-Type Stat5.

Expression vector for murine Stat5a (pXM-Stat5a) was kindly provided by Xiuwen Liu and Lothar Hennighausen (National Institutes of Health, Bethesda, Md.) (14). A dominant-negative (DN) variant of Stat5 (Stat5aΔ713) was derived by truncation after amino acid residue Ala713 of pXM-Stat5a, using a PCR fragment generated using 5'-TAATAC-GACTCACTATAGGG-3' (sense) and 5'-GCTCTAGAC-TAGGCATCTGTGGATGCATTG-3' (antisense) primers, followed by EcoRI and XbaI digestion, and subcloning into the EcoRI-XbaI-digested pXM-Stat5a. The DNA sequence of the resulting construct pXM-Stat5aΔ713 was verified before use. The ability of our DNStat5 (Stat5aΔ713) expression construct to completely suppress both Stat5a and Stat5b-mediated transcriptional activation has been reported (18). Replication-defective human adenovirus (Ad5) carrying wild-type Stat5 (WTStat5) or DNStat5 was generated using the AdEasy Vector system (Qbiogene, Carlsbad, Calif.). The open reading frame sequences of DNStat5 and WTStat5 were released from respective plasmids by 1) digestion with EcoRI, 2) blunt-ending by Klenow DNA polymerase, and 3)

digestion with HindIII, and the resulting fragments were subcloned into the Klenow DNA polymerase blunt-ended BglII site and the unmodified HindIII site of the pShuttle-CMV transfer vector. Homologous recombination of WTStat5 or DNStat5 transfer vectors with the pAdEasy vector was performed in BJ5183 E. coli by electroporation. Recombined clones were screened by Kanamycin-resistant growth, and confirmed by PacI digestion to yield two bands of 30 kb and 4.5 kb. The recombinant viruses were packaged in QBI-293A cells and resulting clones were selected from plaques and amplified. Expression of WTStat5 and DNStat5 from adenoviral stocks was verified by Western blotting using an anti-panStat5 antibody (Transduction Laboratories, Lexington, Ky.). Selected recombinant viral stocks were expanded in large-scale cultures, purified by double cesium chloride gradient centrifugation, and titered side-by-side by a standard plaque assay method in QBI-293A cells as per the manufacturer's instructions.

Protein Solubilization and Immunoblotting.

Pellets of prostate cancer cells were solubilized in lysis buffer (10 mM Tris-HCl, pH 7.6, 5 mM EDTA, 50 mM sodium chloride, 30 mM sodium pyrophosphate, 50 mM sodium fluoride, 1 mM sodium orthovanadate, 1% Triton X-100, 1 mM phenylmethylsulfonylfluoride, 5 µg/ml aprotinin, 1 µg/ml pepstatin A, and 2 µg/ml leupeptin). Cell lysates were rotated end-over-end at 4° C. for 60 min, and insoluble material was pelleted at 12,000×g for 30 min at 4° C. For immunoprecipitations, the protein concentrations of clarified cell lysates were determined by simplified Bradford method (Bio-Rad Laboratories, Hercules, Calif.). The proteins were analyzed by SDS-polyacrylamide gel electrophoresis and immunoblotting using polyvinylidene difluoride membranes (Millipore, Bedford, Mass.). Blots were exposed overnight to primary antibodies diluted in blocking buffer at the following concentrations: anti-phosphotyrosine-Stat5a/b (Y694/Y699) mAb (Advantex BioReagents, Tex., Conroe; 1 µg/ml ), anti-panStat5mAb (Transduction Laboratories, Inc., Lexington, Ky.; 1 µg/ml) or polyclonal antisera to Stat5a (1:3,000) or Stat5b (1:3,000). The blots were washed in washing buffer [50 mM Tris-HCl (pH 7.6), 200 mM NaCl, 0.25% Tween 20], and incubated with horseradish peroxidase-conjugated goat antibodies to mouse or rabbit IgG (Transduction Laboratories) (5 µg/ml). Enhanced chemiluminesence substrate (Amersham Pharmacia Biotech, Piscataway, N.J.) was used according to the manufacturer's instructions for antibody detection.

Cell Viability Assay.

Cell viability was determined by a colorimetric assay in which a tetrazolium compound is bioreduced by cells into a colored formazan product in direct proportion to the number of living cells in culture (Promega, Wis.). Prostate cancer cells were plated on 96-well plates (10 000 cells/well) and infected the next day with different MOIs (multiplicity of infection) of adenovirus carrying either WTStat5, DNStat5 or LacZ. Cells infected with empty control virus or mock-infected cells served as additional controls. Three days after the infection the assay was performed according to the manufacturer's instructions and the absorbance was recorded at 490 nm.

Cell Death Elisa Assay.

Fragmentation of DNA after cell death induced by inhibition of transcription factor Stat5 was determined by photometric enzyme-immunoassay (Cell Death Detection ELISA$^{PLUS}$; Roche Molecular Biochemicals, Indianapolis, Ind.). Prostate cancer cells were plated on 6-well plates and infected next morning with adenovirus carrying either DNStat5, WTStat5, LacZ, or with empty control virus. Cells were scraped and centrifuged at 200×g, and cytoplasmic fractions containing fragmented DNA were transferred to streptavidin-coated microtiter plates that had been incubated with biotinylated monoclonal anti-histone antibody. The amount of fragmented DNA of nucleosomes bound to anti-histone antibody was evaluated by peroxidase conjugated monoclonal anti-DNA antibody using ABTS as a substrate at 405 nm.

Flow Cytometry.

CWR22Rv and LnCap cells ($1\times10^6$ cells/sample) were washed once in PBS, trypsinized, pelleted at 1,000×g, and washed once in 5 ml of cold PBS. After a second centrifugation, cells were resuspended in 0.5 ml of cold PBS and fixed by dropwise addition of 1.5 ml cold 100% ethanol, while slowly vortexing the cell suspension. After having been fixed for 1 h at 4° C., cells were stained with 100 µg/ml propidium iodide (Roche Molecular Biochemicals) and treated with RNase A (Invitrogen, Carlsbad, Calif.) for 30 min at 37° C. The cells were analyzed by flow cytometry using a Coulter EPICS XL cell analyzer (Beckman-Coulter, Brea, Calif.).

Caspase-3 and Caspase-9 Activity Assays.

Activation of Caspase-3 (Roche Molecular Biochemicals) and Caspase-9 (Oncogene Research Products, Boston, Mass.) were determined by fluorometric enzyme assays. Prostate cancer cells were plated on 6-well plates and infected next morning with adenovirus carrying either DNStat5, WTStat5, LacZ or with empty control virus. Cells were scraped and centrifuged at 500×g, and cytoplasmic fractions containing activated Caspases were transferred to microtiter plates. Caspase-3 substrate (DEVD) or Caspase-9 substrate (LEHD) labeled with the fluorescent molecule 7-amino-4-trifluoromethyl coumarin (AFC) were added to the samples. Free fluorescent AFC was generated proportionally to the amount of activated Caspase in the cell lysate due to proteolytic cleavage of the substrate and determined fluorometrically at 505 nm.

Results and Discussion

Stat5 is frequently activated in human prostate cancer.

Figure 1:
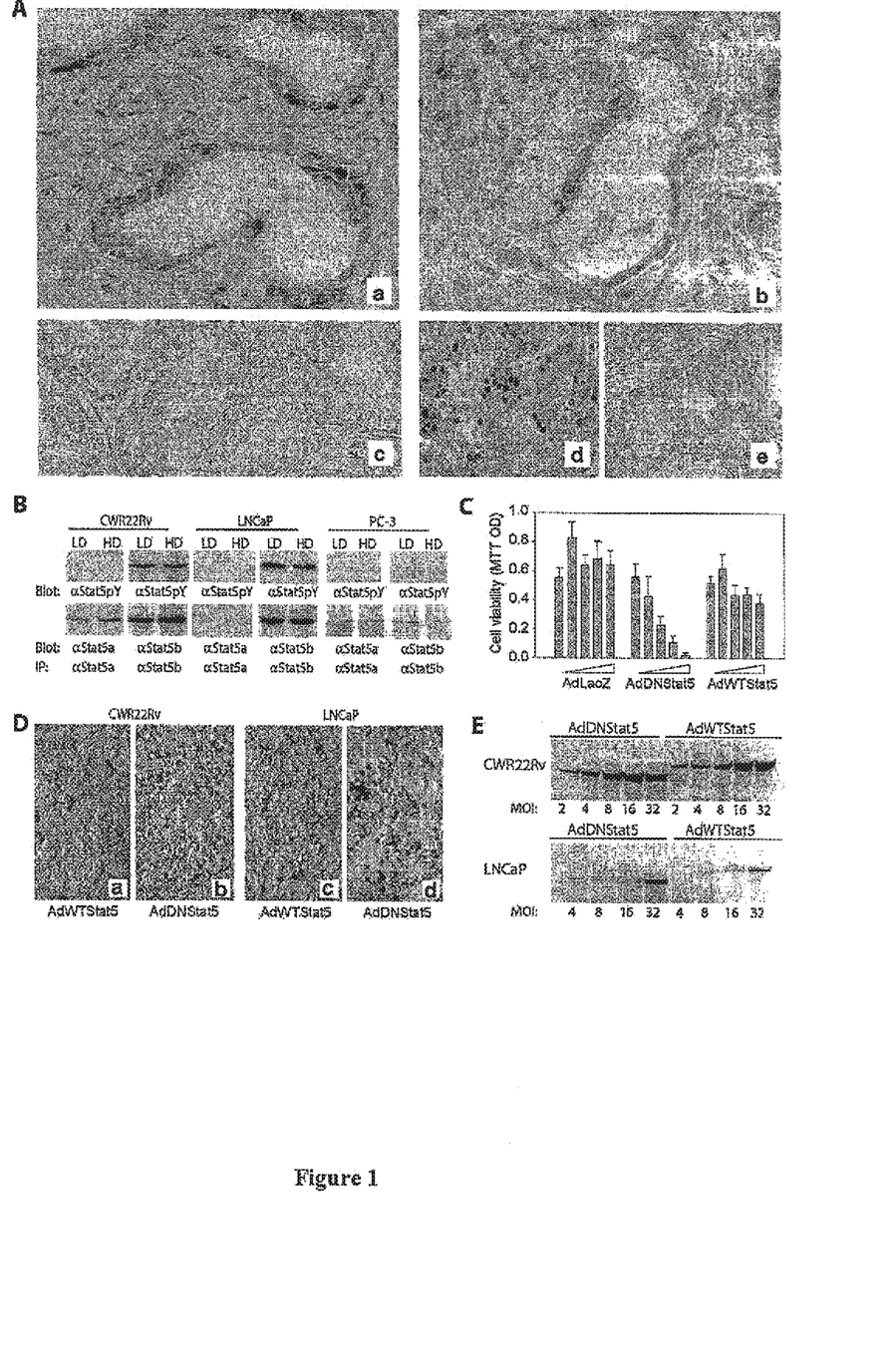
FIG. 1A. Stat5 is activated in human prostate cancer. Detection of activated Stat5 in prostate cancer by immunohistochemical analysis using either anti-phosphoTyrStat5 antibody (panel a) or a pan-Stat5 antibody to detect nuclear localized Stat5 (panel b). Anti-phosphoTyrStat5 staining was negative in normal, secretory human prostate epithelium (panel c). Positive control staining was obtained from normal human breast tissue (panel d) and parallel sections stained with subtype-specific mouse IgG were negative (e).
FIG. 1B. Stat5 is expressed and activated in human prostate cancer cell lines CWR22Rv and LnCap, but not in PC-3. Protein immunoblotting was performed as indicated with either anti-phosphoTyrStat5 (anti-Stat5pY), anti-Stat5a, or anti-Stat5b on immunoprecipitated (IP) Stat5a or Stat5b from lysed prostate cancer cells that had been harvested during exponential growth (low-density; LD) or at confluency (high density; HD).
FIG. 1C. Adenoviral delivery of dominant-negative Stat5 (AdDNStat5) induced cell death in androgen-independent CWR22Rv human prostate cancer cells. Representative experiment showing a dose-dependent effect on cell viability of adenoviral gene delivery of a dominant-negative Stat5 mutant (AdDNStat5) introduced into CWR22Rv cells. AdStat5WT and AdLacZ served as controls. The increasing viral doses used were 0, 1, 2.5, 5, and 10 MOI, and cell viability was measured after 96 h by the MTT metabolic activity assay. Error bars indicate SD of triplicate determinations.
FIG. 1D. Morphology of cell death induced by AdDNStat5 in CWR22Rv and LnCap cells is consistent with apoptosis. Microphotography of AdWTStat5 or AdDNStat5-treated CWR22Rv (72 h, MOI 8) and LnCap cells (96 h, MOI 16).
FIG. 1E. Efficiency of adenoviral delivery of Stat5 proteins into CWR22Rv and LnCap cells. Dose-dependent expression of WTStat5 or DNStat5 in CWR22Rv and LnCap cells as detected by anti-panStat5 immunoblotting of whole cell lysates after 24 h of adenoviral exposure.

Applicants have recently described a highly sensitive in situ detection method for activation of Stat5 in paraffin embedded tissue which is based on immunohistochemical detection of phosphorylated Stat5 that is localized within the cell nucleus (10,17). This method, complemented with immunohistochemical detection of nuclear Stat5 protein, was applied to a material of 40 human prostate cancer specimens, and significant activation of Stat5 was detected in 65% (26 of 40) of primary human prostate cancer specimens of various Gleason scores. Representative samples illustrating Stat5 activation by either phosphotyrosine detection, or nuclear anti-Stat5 detection, within malignant human prostate epithelia are presented (FIG. 1A, panels a and b, respectively). In contrast, Stat5 phosphotyrosine staining was negative (FIG. 1A, panel c) and nuclear immunostaining for Stat5 was absent in adjacent normal secretory prostate epithelial cells. Lactating human breast epithelium is presented as a positive control for tyrosine phosphorylated, activated human StatS (17), and parallel sections of lactating human breast stained with subtype-specific mouse IgG were negative (FIG. 1A, panels d and e, respectively).

Stat5 is activated in CWR22Rv and LnCap cell lines, but not in PC-3 cells.

Next, Applicants examined Stat5a and Stat5b protein expression and activation in three human prostate cancer cell lines, including the androgen-independent CWR22Rv and PC-3 cells, and the androgen-sensitive LnCap cell line. For this analysis, immunoprecipitation of either Stat5a or Stat5b was followed by immunoblotting with the anti-phosphoTyrStat5 antibody or with antibodies to either Stat5a or Stat5b. Stat5b was the predominant Stat5 protein expressed in CWR22Rv and LnCap cells both during exponential growth (low density; LD) and in confluent culture conditions (high density; HD; FIG. 1B). In both CWR22Rv and LnCap cells at low and at high cell density, Stat5b was phosphorylated on the critical Y699 residue. In contrast, no activation of Stat5a or Stat5b was detected in PC-3 cells, consistent with low or undetectable levels of Stat5 protein in these cells (FIG. 1B).

Blocking of Stat5 activity in human prostate cancer lines induces cell death.

Based on the prevalent activation of Stat5 in human prostate cancer tissues, Applicants hypothesized that Stat5 may act as a survival protein in human prostate cancer. Therefore, Applicants tested whether blocking Stat5 function in human prostate cancer cells would induce cell death. To block activated endogenous Stat5 proteins in human prostate cancer, Applicants generated an adenovirus for effective delivery of a dominant-negative mutant of Stat5 (DNStat5), and a matching control virus carrying wild type (WT) Stat5. The molecular construction of the adenoviral vector carrying dominant-negative Stat5a (AdDNStat5) and the matching control, AdWTStat5, is described in the Materials and Methods section (See Example 2). Truncation of Stat5a after amino acid 713 removes the entire transcriptional activation domain, and generates a Stat5a mutant that is almost identical to the corresponding Stat5b truncated form. As expected, the Stat5a mutant effectively blocked the function of both WT Stat5a and Stat5b (18). Applicants have further validated both the AdDNStat5 and the AdWTStat5 viral constructs in functional assays, including assays for gene induction, inducible tyrosine phosphorylation, and DNA binding.

To determine whether blocking endogenous Stat5 activity would induce death of human prostate cancer cells, Applicants first examined the effect of increasing doses of AdDNStat5 on the viability of the androgen-independent CWR22Rv cell line. For the initial cell viability studies Applicants used an assay determining the metabolic activity of the cells. CWR22Rv cells were cultured to 70% confluence in 96-well plates, and exposed for 90 min to AdDNStat5 or AdWTStat5 at doses up to MOI 10, after which the virus was diluted 6-fold in culture medium as described. After 96 h of infection, cells were analyzed for cell viability. A marked and dose-dependent effect of the expression of DNStat5 on. cell viability was observed, with detectable suppression at MOI 2.5, and suppression of cell viability by more than 90% at MOI 10 (FIG. 1C). In contrast, cells infected with AdWTStat5 or AdLacZ did not show significant loss of viability (FIG. 1C). Viability of CWR22Rv cells infected with an empty control virus (AdCtrl) was not reduced (not shown). The selective effect of AdDNStat5 in CWR22Rv cells was consistently observed in experiments that were repeated and reproduced more than five times, and with four different, independently titered batches of virus.

Prostate cancer cell death induced by DNStat5 represents apoptosis.

Microscopic assessment of the effect of AdDNStat5 on CWR22Rv cell viability confirmed extensive cell death following expression of DNStat5. CWR22Rv cells exposed to AdDNStat5 at MOI 8 for 72 h displayed extensive cell death as evidenced by cell rounding, detachment, shrinkage, and blebbing (FIG. 1D, panel b), which are morphological changes consistent with apoptotic cell death. In contrast, there was no evidence of reduced cell viability in response to AdWTStat5 (FIG. 1D, panel a). Likewise, AdDNStat5, but not AdWTStat5, induced cell death also in the androgen-sensitive human prostate cancer cell line, LnCap (FIG. 1D, panels c and d). Dose response analyses showed that 2-4 fold higher doses of virus were needed to induce cell death in LnCap cells compared to CWR22Rv cells (not shown), an effect that correlated with less efficient adenoviral gene delivery of Stat5 proteins into LnCap cells. Specifically, dose-response analyses of viral protein delivery revealed that the same amount of virus induced lower levels of DNStat5 or WTStat5 expression in LnCap cells than in CWR22Rv cells shown by immunoblotting of whole cell lysates (FIG. 1E). FIG. 1E also indicates that cellular levels of DNStat5 and WTStat5 delivered by the respective adenoviral vectors are comparable, supporting the notion that the selective cell death observed in response to AdDNStat5 is due to its specific dominant-negative characteristics and not caused by other nonspecific mechanisms. In contrast, there were no signs of cell death in PC-3 cells after 72 h exposure to AdDNStat5 at MOI 32 as judged from cell morphology.

Figure 2:
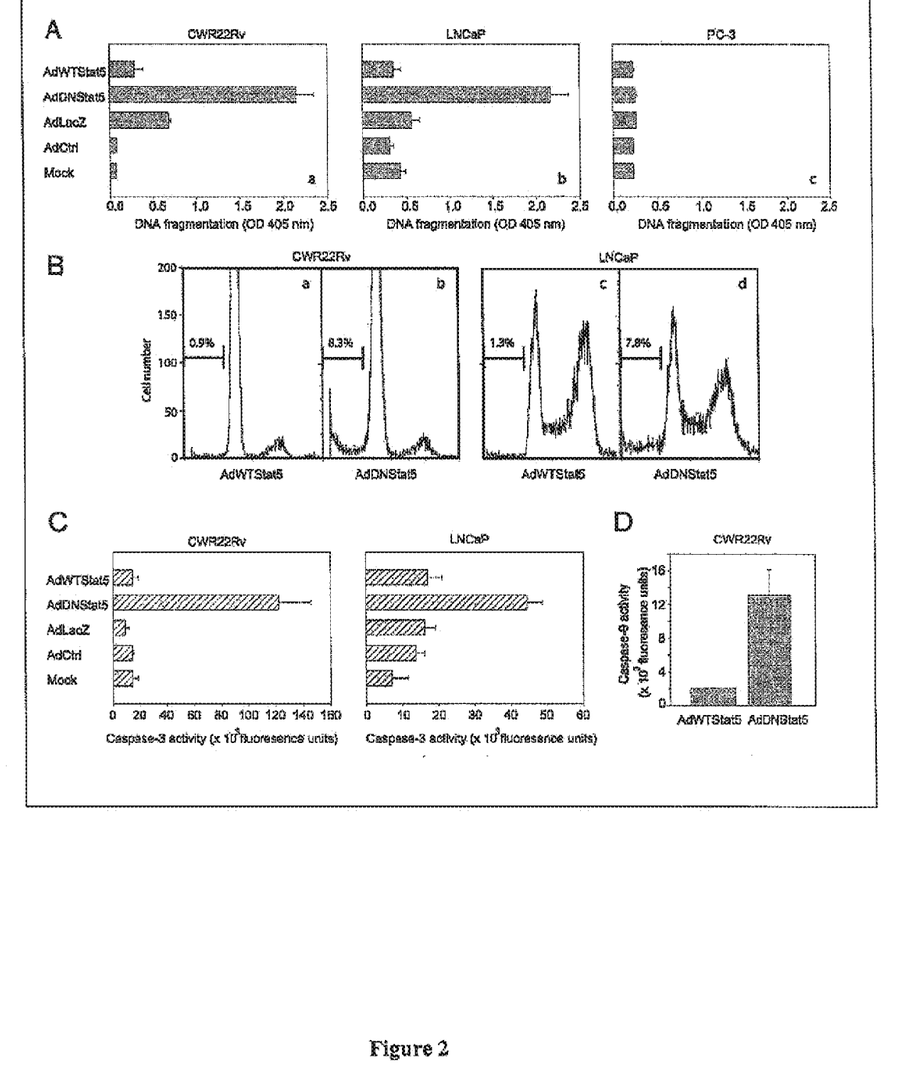
FIG. 2A. DNStat5-induced fragmentation of DNA in human prostate cancer lines CWR22Rv and LnCap, but not PC-3. DNA fragmentation analyzed by nucleosomal ELISA after exposure to AdDNStat5, AdWTStat5, AdLacZ, AdCtrl, or mock infection in CWR22Rv (48 h, MOI 8), LnCap cells (72 h, MOI 32), or PC-3 cells (72 h, MOI 32). A representative experiment of six independent repeats is shown; error bars represent SD of triplicate determinations.
FIG. 2B. DNStat5 induced apoptosis in CWR22Rv and LnCap cells as determined by flow cytometry. Cellular apoptosis detected as increased hypodiploid fraction after treatment with AdDNStat5 or AdWTStat5, AdLacZ, AdCtrl, or mock infection in CWR22Rv (48 h, MOI 8), LnCap cells (72 h, MOI 32). The respective fractions of hypodiploid cells for CWR22Rv cells treated with AdLacZ, AdCtrl, or Mock, were less than 1.5% for both CWR22Rv and LnCap cells.
FIG. 2C. DNStat5-induced apoptosis is associated with Caspase-3 activation. Caspase-3 activation was determined after exposure to AdDNStat5 and control conditions as indicated in CWR22Rv (36 h, MOI 8) and LnCap cells (48 h, MOI 32). A representative experiment of three independent repeats is shown; error bars represent SD of triplicate determinations.
FIG. 2D. DNStat5-induced Caspase-3 activation is associated with activation of Caspase-9. CWR22Rv cells exposed to DNStat5 showed activation of Caspase-9 at 36 h after initiation of treatment. A representative experiment of three independent repeats is shown; error bars represent SD of triplicate determinations.

To further verify that DNStat5-induced killing of prostate cancer cells was due to apoptotic cell death, prostate cancer cells were analyzed for DNStat5-induced fragmentation of DNA. CWR22Rv cells were exposed to AdDNStat5 and a set of controls at MOI 8 for 48 h. A selective effect of DNStat5 on induction of DNA fragmentation was observed, as analyzed by an enzyme-linked immunosorbent assay (ELISA) of nucleosomal DNA fragments (FIG. 2A, panel a). On average, a seven-fold increase in nucleosomal DNA fragmentation was detected in cells exposed to AdDNStat5 over that detected in WTStat5 expressing cells (6 repeats, each with 3 replicates/treatment group). Furthermore, DNStat5-induced death of LnCap cells was also associated with DNA fragmentation, as evidenced by a consistent and more than six-fold increase in DNA fragmentation over levels in AdWTStat5 treated cells on day 3 at MOI 32 (FIG. 2A, panel b) (6 repeats, each with 3 replicates/treatment group). Therefore, Applicants conclude that suppression of Stat5 induces apoptotic cell death in both CWR22Rv and LnCap cells, as revealed by fragmentation of DNA. In contrast, exposure of PC-3 cells, which do not express active Stat5, to AdDNStat5 did not increase fragmentation of DNA when compared to cells expressing WTStat5 or to cells infected with empty control virus, AdLacZ, or mock-infected cells (FIG. 2A, panel c).

Apoptotic cell death of prostate cancer cells expressing DNStat5 was also verified by cell cycle analysis. In both CWR22Rv and LnCap cells expressing DNStat5, but not in cells expressing AdWTStat5, extensive DNA fragmentation was detected in the form of a large fraction of hypodiploid cell fragments (FIG. 2B). In CWR22Rv cells, this proportion was estimated to be approximately 8% of total cellular DNA at Day 3 of AdDNStat5 infection using MOI of 8, which was 8-fold higher than that observed in parallel AdWTStat5-treated cells (0.9%). In LnCap cells, the fraction of cell fragments with hypodiploid DNA content increased 6-fold from 1.3% in AdWTStat5-treated cells to approximately 8% in DNStat5-treated cells. Mock-infected cells and cells infected with empty control virus or AdLacZ were used as controls, and the fraction of hypodiploid cells consistently remained below 1.3%.

DNStat5-induced apoptosis of CWR22Rv and LnCap cells involves Caspase-3 activation.

Proteolytic enzymes of the caspase family are critical mediators of programmed cell death. A central role has been ascribed to Caspase-3 as a key executor of a major category of apoptotic cell death (19). To determine whether apoptosis in prostate cancer cells induced by expression of DNStat5 is mediated by activation of Caspase-3, Applicants analyzed Caspase-3 activation by a specific Caspase-3 enzymatic assay. Exposure of CWR22Rv or LnCap cells to AdDNStat5 for 36 h or 48 h, respectively, activated Caspase-3 in both cell lines (FIG. 2C). Specifically, in CWR22Rv cells, activation of Caspase-3 was increased 8-fold in cells expressing DNStat5 compared to AdWTStat5-infected cells. In LnCap cells the corresponding increase was approximately 2-fold (3 repeats each with 3-replicates/treatment group). Therefore, Applicants conclude that DNStat5-induced apoptosis in both CWR22Rv and LnCap human prostate cancer cells involved activation of Caspase-3.

Caspase-3 mediated apoptosis may be induced through upstream activation of Caspase-9 in a Cytochrome C-dependent manner, or through Caspase-9 independent mechanisms (20). Since suppression of Stat5 activation in CWR22Rv and LnCap cells induced activation of Caspase-3, Applicants wanted to determine whether DNStat5-induced activation of Caspase-3 involved activation of Caspase-9. Caspase-9 activity was monitored in response to DNStat5 in both CWR22Rv and LnCap cells for up to 72 h. A 6-fold induction of Caspase-9 was detected at 36 h in CWR22Rv cells expressing DNStat5 (FIG. 2D). In LnCap cells, the same trend was observed, but the effect was less striking. Applicants conclude that DNStat5-induced cell death in CWR22Rv cells is mediated by Caspase-3 through a Caspase-9 dependent mechanism. Caspase-9 activation further indicates a cytochrome C/Apaf-1 dependent apoptotic process (20).

The prevalent detection of activated Stat5 in primary human prostate cancer specimens indicates that Stat5 is a candidate therapeutic target in a high proportion of prostate cancers. A recent study by Gao and colleagues indicated that in human prostate tissue homogenates there was only a low level of Stat5 binding to an oligonucleotide probe corresponding to the Stat5 response element of the rat beta-casein promoter in electrophoretic mobility shift assays (21). It is possible that prostate cancer-specific or stromal factors interfere with binding of Stat5 to this promoter when whole tissues are homogenized. In this regard, using a highly sensitive in situ technique, which detects Stat5 activation at a single cell level, Applicants have recently demonstrated that Stat5 is activated in normal human and mouse mammary epithelial cells outside of pregnancy, an activity that is difficult to detect by EMSA using tissue homogenates of whole mammary glands (17).

The present work suggests that blocking activation of Stat5 in human prostate is a potential new therapeutic approach. Delivery of suicide genes into cancer cells is hampered by lack of effective delivery systems, but gene therapeutic delivery systems are constantly improving and involve both viral and non-viral strategies (22,23). Future prostate cancer gene therapy based on delivery of DNStat5 may therefore be feasible. On the other hand, small molecule inhibitors of the Stat5 tyrosine kinase(s) responsible for Stat5 activation in prostate cancer could represent an alternative and more effective approach to inhibit Stat5 in human prostate cancer with even more attractive pharmacological characteristics. Jak2 tyrosine kinase is a candidate target, since this enzyme is responsible for tyrosine phosphorylation of Stat5 by a series of cytokine receptors, including receptors for prolactin (Prl). Prl-receptor associated signaling pathways are of particular interest, because Prl is produced locally in prostate epithelium indicating an autocrine loop of Prl action in prostate (1,8). In addition to Jak2, other tyrosine kinases, such as Jak1, Jak3 or Tyk2, as well as members of the Src tyrosine kinase family, or receptor tyrosine kinases, are also possible Stat5 kinases in prostate cancer (24).

Applicants show using in situ detection of phosphorylated and nuclear Stat5 that Stat5 was activated in a majority of prostate cancer specimens examined. This suggests that inhibition of Stat5 as a therapeutic approach could have a broad usefulness in the treatment of prostate cancer. The observation that both androgen-refractory CWR22Rv and androgen-sensitive LnCap cells responded to suppression of Stat5 with cell death, implies that apoptosis induced by blocking the activation of Stat5 is independent of responsiveness to androgens. Furthermore, the correlation between endogenous Stat5 activation in prostate cancer cell lines and their sensitivity to DNStat5 indicates that immunohistochemical detection of activated Stat5 in prostate cancer may predict responsiveness to this therapeutic strategy.

REFERENCES

1. Nevalainen, M. T., Valve, E. M., Ingleton, P. M., Nurmi, M., Martikainen, P. M., and Harkonen, P. L. (1997) *J Clin Invest* 99(4), 618-27.
2. Nevalainen, M. T., Valve, E. M., Makela, S. I., Blauer, M., Tuohimaa, P. J., and Harkonen, P. L. (1991) *Endocrinology* 129(2), 612-22.
3. Nevalainen, M. T., Härkönen, P. L., Valve, E. M., Ping, W., Nurmi, M., and Martikainen, P. M. (1993) *Cancer Res* 53, 5199-5207
4. Ahonen, T. J., Harkonen, P. L., Laine, J., Rui, H., Martikainen, P. M., and Nevalainen, M. T. (1999) *Endocrinology* 140(11), 5412-21.
5. Wennbo, H., Kindblom, J., Isaksson, O. G., and Tornell, J. (1997) *Endocrinology* 138(10), 4410-5.
6. Kindblom, J., Dillner, K., Ling, C., Tornell, J., and Wennbo, H. (2002) *Prostate* 53(1), 24-33.
7. Steger, R. W., Chandrashekar, V., Zhao, W., Bartke, A., and Horseman, N. D. (1998) *Endocrinology* 139(9), 3691-5.
8. Nevalainen, M. T., Valve, E. M., Ahonen, T., Yagi, A., Paranko, J., and Harkonen, P. L. (1997) *Faseb J* 11(14), 1297-307.
9. Nevalainen, M. T., Valve, E. M., Ingleton, P. M., and Harkonen, P. L. (1996) *Endocrinology* 137(7), 3078-88.
10. Ahonen, T. J., Harkonen, P. L., Rui, H., and Nevalainen, M. T. (2002) *Endocrinology* 143(1), 228-38.
11. Nevalainen, M. T., Ahonen, T. J., Yamashita, H., Chandrashekar, V., Bartke, A., Grimley, P. M., Robinson, G. W., Hennighausen, L., and Rui, H. (2000) *Lab Invest* 80(7), 993-1006.
12. Darnell, J. E., Jr. (1997) *Science* 277(5332), 1630-5
13. Wakao, H., Gouilleux, F., and Groner, B. (1994) *Embo J* 13(9), 2182-91.
14. Liu, X., Robinson, G. W., Gouilleux, F., Groner, B., and Hennighausen, L. (1995) *Proc Natl Acad Sci USA* 92(19), 8831-5.
15. Rui, H., Kirken, R. A., and Farrar, W. (1994) *J Biol Chem* 269, 5364-5368
16. Gouilleux, F., Wakao, H., Mundt, M., and Groner, B. (1994) *Embo J* 13(18), 4361-9.
17. Nevalainen, M. T., Xie, J., Bubendorf, L., Wagner, K. U., and Rui, H. (2002) *Mol Endocrinol* 16(5), 1108-24.
18. Yamashita, H., Iwase, H., Toyama, T., and Fujii, Y. (2003) *Oncogene* 22(11), 1638-52.
19. Budihardjo, I., Oliver, H., Lutter, M., Luo, X., and Wang, X. (1999) *Annu Rev Cell Dev Biol* 15, 269-90
20. Leist, M., and Jaattela, M. (2001) *Nat Rev Mol Cell Biol* 2(8), 589-98.
21. Ni, Z., Lou, W., Lee, S. O., Dhir, R., DeMiguel, F., Grandis, J. R., and Gao, A. C. (2002) *J Urol* 167(4), 1859-62.
22. Mah, C., Byrne, B. J., and Flotte, T. R. (2002) *Clin Pharmacokinet* 41(12), 901-11

23. Niidome, T., and Huang, L. (2002) *Gene Ther* 9(24), 1647-52.
24. Grimley, P. M., Dong, F., and Rui, H. (1999) *Cytokine Growth Factor Rev* 10(2), 131-57.

Incorporation By Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of inhibiting prostate cancer cell growth, comprising inhibiting Stat5 activity in prostate cancer cells, wherein Stat5 activity is inhibited by contacting the prostate cancer cells with a small molecule that inhibits Stat5 activity or with an antibody that binds to a Stat5 polypeptide and inhibits Stat5 activity.

2. The method of claim 1, wherein the small molecule is an inhibitor of a Stat5 tyrosine kinase that activates Stat5 in prostate cancer cells, or the antibody inhibits activation of Stat5 by a Stat5 tyrosine kinase in prostate cancer cells.

3. The method of claim 2, wherein the Stat5 tyrosine kinase is Jak1, Jak2, Jak3, Tyk2, Src, Fyn, Yes, Lck, Hck, Blk, Fgr or Lyn.

4. The method of claim 1, wherein the inhibition of Stat5 activity in the prostate cancer cells results in prostate cancer cell death.

5. The method of claim 1, wherein the prostate cancer is primary prostate cancer, advanced prostate cancer or metastatic prostate cancer.

6. A method of treating prostate cancer in a male in need of such treatment, comprising administering to the male a therapeutically effective amount of a small molecule that inhibits Stat5 activity in prostate cancer cells of the male or a therapeutically effective amount of an antibody that binds to a Stat5 polypeptide and inhibits Stat5 activity in prostate cancer cells of the male.

7. The method of claim 6, wherein the small molecule is an inhibitor of a Stat5 tyrosine kinase that activates Stat5 in prostate cancer cells, or the antibody inhibits activation of Stat5 by a Stat5 tyrosine kinase in prostate cancer cells.

8. The method of claim 7, wherein the Stat5 tyrosine kinase is Jak1, Jak2, Jak3, Tyk2, Src, Fyn, Yes, Lck, Hck, Blk, Fgr or Lyn.

9. The method of claim 6, wherein the inhibition of Stat5 activity in the prostate cancer cells results in prostate cancer cell death.

10. The method of claim 6, wherein the prostate cancer is primary prostate cancer, advanced prostate cancer or metastatic prostate cancer.

11. A method of diagnosing or aiding in the diagnosis of prostate cancer in a male, comprising:

(a) obtaining a prostate tissue sample from a male; and (b) determining whether activated Stat5 is present in cells of the prostate tissue sample, wherein the presence of activated Stat5 is an indication of prostate cancer in the male.

12. The method of claim 11, wherein the prostate cancer is primary prostate cancer, advanced prostate cancer or metastatic prostate cancer.

13. The method of claim 11, wherein the presence of activated Stat5 in (b) is detected by a method selected from the group consisting of: immunohistochemistry, immunocytochemistry and DNA-binding assays.

14. The method of claim 11, wherein the activated Stat5 in (b) is nuclear Stat5.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
taatacgact cactataggg                                          20

<210> SEQ ID NO 2
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 2
gctctagact aggcatctgt ggatgcattg                               30
```